United States Patent [19]

Verret

[11] Patent Number: 4,485,675
[45] Date of Patent: Dec. 4, 1984

[54] PNEUMATIC FLUID DENSIOMETER

[76] Inventor: Willie M. Verret, Rte. 2, Box 425G, St. Martinville, La. 70582

[21] Appl. No.: 419,157

[22] Filed: Sep. 17, 1982

[51] Int. Cl.³ .............................................. G01N 9/26
[52] U.S. Cl. ...................................................... 73/439
[58] Field of Search .......................... 73/438, 439, 302

[56] References Cited

U.S. PATENT DOCUMENTS

| | | | |
|---|---|---|---|
| 804,570 | 11/1905 | Wheeler | 73/302 |
| 2,910,871 | 11/1959 | Dower | 73/438 |
| 3,541,989 | 11/1970 | Leonard | 73/439 X |
| 3,911,741 | 10/1975 | Rochon et al. | 73/439 X |
| 4,006,636 | 2/1977 | Holmen | 73/302 |

Primary Examiner—James J. Gill
Attorney, Agent, or Firm—Thomas S. Keaty

[57] ABSTRACT

A device for determining the density of drilling mud by having one end of a float carried tube 8.34 inches below the surface of the mud. A constant flow of air is supplied to the other end of the tube. The pressure of the air entering the tube, when air bubbles appear at the surface of the mud, is indicative of the density. The tube is maintained vertical by passing the tube through the grooves of a group of pulley wheels.

11 Claims, 3 Drawing Figures

PNEUMATIC FLUID DENSIOMETER

BACKGROUND OF THE INVENTION

1. Field of the Invention

The present invention relates to an apparatus for measuring the weight of fluids, particularly for determining the weight of drilling, completion, and workover fluids used in drilling, completion, and workover operations in the context of oil well drilling operations.

2. Background of the Invention

The present invention relates to an improved apparatus for accurately determining the unit weight of drilling fluid being pumped into a well during drilling operations and for determining the weight of the drilling fluid returning from the well during drilling operations. Also, present invention can be used to similarily determine the unit weight of drilling fluid being utilized in completion and workover operations within the context of oil well drilling operations.

During the drilling of a well in the quest for hydrocarbons using the rotary method of drilling, it is necessary to pump or circulate a drilling fluid, known in the art as "drilling mud", downwardly through the drill pipe to which the drill bit is attached and outwardly through the drill bit into the annulus formed by the drill pipe and the wall of the well bore, for return upwardly through the annulus to the surface.

A container known as a suction tank contains the drilling fluid for pumping through the drill pipe into the well. Circulating drilling mud exits from the drill bit returning to the surface through the annulus between the drill pipe and the wall of the well bore and out into a shaker box where the cuttings which are drilled up are separated from the returning drilling fluid. Drilling fluid then flows from the shaker box via a settling tank back to the suction tank for return to the well. Drilling mud is essential to a well drilling operation as it serves to carry away the cuttings from the drill bit to facilitate drilling and act as a medium for transporting the cuttings from the drill bit area out of the well bore to be separated from the mud by means of the shaker box or settled out in a mud pit at the top of the well prior to recirculation. The primary function of the drilling mud is to act as a stopper in the well by exerting hydrostatic pressure on the bottom of the well according to the specific weight of the drilling mud thereabove to balance or overcome the formation pressure in order to prevent blowouts. The pressure of the formation adjacent to the drill bit, or bottom-hole pressure, must also be taken into consideration because this pressure must be sufficient to sustain the hydrostatic pressure of the mud in order to prevent loss of circulation, and loss of the mud as it escapes into the formation due to the pressure exerted by the mud column being substantially greater than the formation pressure itself. It is therefore essential that the pressure of the well bore, i.e., formation pressure, and the hydrostatic pressure of the drilling mud be maintained near balanced condition. The drilling mud also acts as a sealing means upon the well bore by caking on the surface of the bore to seal the bore and prevent the drilling mud from flowing out into the formation material.

It is necessary that the drilling mud be of sufficient weight to balance against the force of any upwardly acting hydrostatic pressure such as the pressure of gas, water, or oil which may be exposed in drilling and, at the same time, the drilling mud should not become so heavy that it enters the formation causing a loss of circulation. As conditions vary in the course of drilling, the weight of the drilling mud has to be altered to meet these changing conditions. For instance, if the gas sand is penetrated, the gas of the bore space will become a part of the drilling fluid. As the fluids are pumped out of the hole the gas expands, with the consequence that the mud flows out of the hole at a faster rate than it enters and the mud weight becomes considerably lighter. Such a condition must be detected immediately as remedial action may be necessary by the addition of weighted material to the drilling fluid, as otherwise the fluid might not contain the forces of the formation pressures reacting upwardly thereagainst with the consequence that a blowout may occur.

The use of excessive mud weight to provide a large factor of safety against blowouts has been previously used as a standard drilling procedure. Of course, as mentioned previously, such an overbalance may result in a loss of circulation where the formation pressures are incapable of withstanding the over-balanced hydrostatic pressures of the drilling mud. For reasons of economy, a new drilling concept of balanced pressure drilling was adopted and it became essential that continual accurate measurement of the mud weight be maintained at all times during the drilling operation, since less dense drilling mud allows faster drilling with less wear on the equipment. Since balanced pressure drilling reduced the factor of safety against blowouts, which resulted from excess mud weight, it becomes imperative that accurate and continuous mud weights into and out of the well be logged since the best evaluation of bottom hole conditions is to continuously determine the absence or to accurately measure the volume of gas entering the hole. Such a determination will provide information essential to maintaining minimal mud weight to balance the bottom hole pressures and prevent blowout conditions.

It is recognized that a continuous accurate measure of the amount of gas entering the formation is valuable information for properly balancing the well during the drilling operation. Drilling for hydrocarbons is hazardous as is evident by frequent blowouts which cause considerable air and water pollution and general ecological damage, which entails considerable expense and delays in the oil rig operation, in addition to causing periodically serious injuries. Blowouts result from the unknown relationship between formation pressures and the weight of the drilling mud which is predetermined for formation pressure containment and penetration control. The mud weight determinations are initially based on historical data for a particular formation which, of course, is only an approximation and it is therefore essential that accurate and continuous determinations be made of the drilling fluid exiting from a well since the mud weight out of the well is a reflection of the bottom hole pressure of the formation being drilled up.

The present invention is an improved apparatus for accurately measuring the weight of the drilling mud being pumped into the well and accurately determining the weight of the mud being pumped out of the well and continuously logging the information on a time chart so that an accurate determination can be made as to changes in the mud weight resulting from bottom hole conditions. The determination of mud weight in and mud weight out require two measurements, one of which is made in the suction tank which contains the drilling fluid being pumped into the well and the other measurement is made in the shaker box which contains the drilling fluid returning from the well. There have been some devices of the prior art which have attempted to make this accurate determination of the weight of the drilling mud, some of these devices of the prior art consisting of a differential pressure densiometer in which the weight of the fluid is measured by the difference in pressure between two pneumatic tubes submerged in the drilling fluid, both tubes having independently controlled air supplies, wherein the pressure of the air in each tube is regulated to the same rate and the flow is metered so that both tubes have the same volume of air at equal pressure flowing into the mud being measured, the ends of the tubes being positioned at exactly 8.35 inches apart, which represents the weight of water in pounds per gallons. Therefore, when the weight of the drilling fluid is increased or decreased, the pressure differential at the ends of the submerged tubes will increase or decrease by one inch of water pressure for each pound per gallon increase or decrease in the weight of the drilling fluid. This permits direct reading in pounds per gallon on a pressure differential recording device. However, these attempts to use pressure differential pneumatic tubes for measuring the weight of the fluid have been highly inaccurate and infeasible in actual practice.

It is the primary object of the present invention to provide an apparatus which accurately and feasibly measures the weight of the drilling mud being pumped into the well and out of the well and for continuously logging the information so that an accurate determination can be made of the changes in the mud weight resulting from bottom hole conditions.

The present invention features a single air pressure sensor tube threaded on top for mating with a connector fitting which is connected to a source of air supply and a remote pressure recorder and pressure gauge. A preferably adjustable float is mounted around the sensor tube to ensure that the sensor tube remains submerged in the fluid within the suction tank or the shaker box at a certain depth, regardless of variations in the level of the drilling fluid in the tank. A pressure gauge which is connected to the connector fitting at the top of the sensor tube above the connection of the air supply hose to the connection fitting at the top of the pressure sensor tube, measures the pressure sensed by the sensor tube in inches of water, preferably, and the remote pressure recorder connected adjacent thereto continuously records the measurements continuously generated by the pressure gauge. The air sensor tube has an open-ended bell bottom with a check valve mounted therein to prevent plugging of the sensor tube in the event the air supply is momentarily lost. The weight of fresh water is 8.34 pounds per gallon. Therefore, as in the preferred embodiment, if the sensor tube is submerged 8.34 inches in fresh water, the air pressure required to maintain air flow through the sensor tube will be 8.34 inches of water as seen on the pressure gauge and recorder. For the purposes of the present invention, this pressure is read as 8.34 pounds per gallon. In operation, the sensor tube is fixedly submersed in the drilling fluid to have its density determined, regardless of the amount of drilling fluid in the suction tank or shaker box, because of the float being fixed 8.34 inches above the bell-bottom. Further, the sensor tube is maintained in a substantially vertical position relative to the surface of the drilling fluid in the suction tank or shaker box, by means of a plurality of pulley wheels rotatably mounted on a plate which is fixably attached to a C-clamp which is securely mounted to the suction tank or shaker box, preferably, so that the sensor tube is allowed to pass between the pulley wheels when the sensor tube is vertical relative to the surface of the drilling fluid to have its density determined, the pulley wheels thereby maintaining the sensor tube in this vertical position relative to the surface of the drilling fluid. This dispositon of the sensor tube in a vertical position relative to the surface of the drilling fluid ensures an accurate reading of the density of the drilling fluid to have its density determined. Now, if the sensor tube is submersed at this 8.34 inches, but in 18.0 pounds per gallon drilling fluid, the amount of air pressure required to maintain air flow will read 18 inches of water on the pressure gauge and recorder. This pressure is interpreted as 18.0 pounds per gallon mud weight.

Because of the use of one sensor tube rather than two sensor tubes, the apparatus of the present invention has proven to achieve more accurate readings and is simpler to implement.

Many other objects and advantages of the present invention will become apparent from the detailed description of the preferred embodiment.

DETAILED DESCRIPTION OF THE PREFERRED EMBODIMENT

Figure 1:
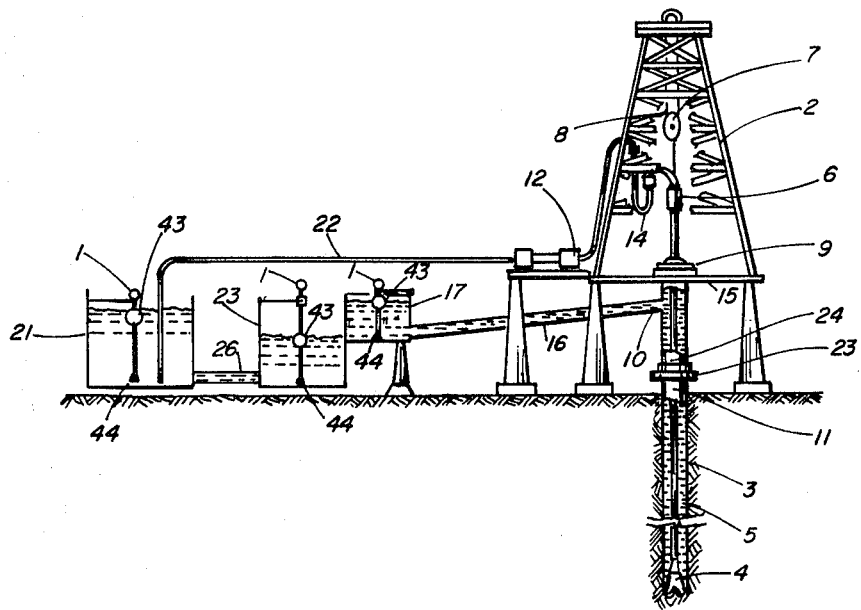
FIG. 1 is a schematic, sectional view of a drilling rig including pumps, well bore, suction tank and shaker box with the present invention included therein.

As can be seen from FIG. 1, a derrick 2 has been illustrated as mounted over the well bore 3 which is being drilled by the drill bit 4 connected to drill pipe 5 which is in turn connected to a swivel 6, a travelling block 7 and the hoisting lines 8. This drill pipe is rotated by rotary table 9 which receives its power from a suitable source. The well bore 3 is being filled with a drilling mud 10 which is forced downwardly by pump 12 through a hose 14 and into the upper end of the drill pipe 5. The mud is picked up by the pump from the suction tank 21 via conduit 22 shown partly in schematic form in FIG. 1. Well casing 11 exits from the bore 3 in known manner and has a blow out preventor 23 mounted on top of said casing with a bell nipple 24 mounted on top of the blow out preventor 23. The drilling mud circulates upwardly in the casing within the annular space between the casing 11 and the drill pipe 5 and will rise to a level such as 15 in the casing depending upon the rate of circulation which is being maintained by the pump 12. The discharge flow line 16 allows the drilling mud to discharge from the well bore and into the shaker box 17. The drilling mud exits from the shaker box over a vibrating screen not shown and into settling tank 25. The drilling fluid then travels from the settling tank 25 via conduit 26 and into the suction tank 21 to be recycled into the well via conduit 22.

Figure 2:
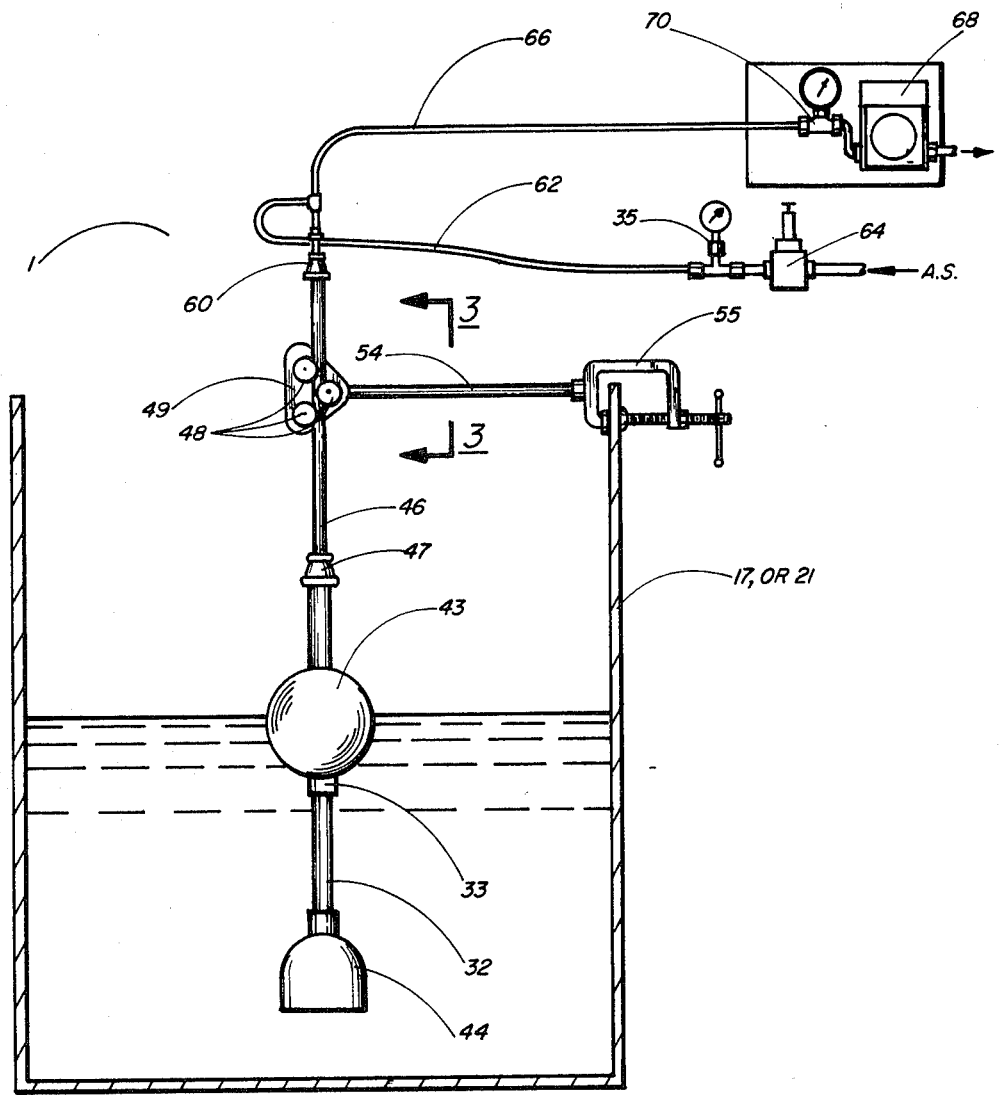
FIG. 2 is a partially schematic, cross-sectional, elevational view of the present invention mounted to the suction tank.
Figure 3:
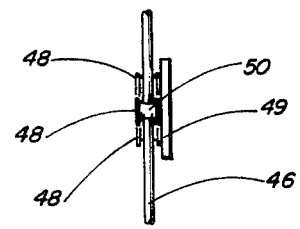
FIG. 3 is a cross-sectional, frontal view of the vertical aligning means of the present invention for maintaining the sensor tube and extension tube in a substantially vertical axis relative to the surface of the drilling fluid.

As shown in FIG. 2, there can be seen the pneumatic fluid densiometer of the present invention, as indicated generally by the numeral 1. The pneumatic fluid densiometer of the present invention comprises a pneumatic tube 32 submersed 8.34 inches in the drilling fluid contained by either the shaker box 17 or the suction tank 21, the pneumatic tube 32, or sensor tube 32 being threadedly connected near its top end, preferably (although it can be fixably attached), to a generally spherical airtight floating chamber 43, or float 43, float 43 being maintained at a distance of 8.34 inches from the bottom end of sensor tube 32 by means of collar 33, thereby ensuring that sensor tube 32 remains constantly sumbersed 8.34 inches in the drilling fluid to have its density determined, for reasons which will hereinafter be seen. Sensor tube 32 comprises an open-ended, generally bell-shaped bottom 44, which can be either threadedly connected or fixably attached to the bottom end of sensor tube 32. The top end of sensor tube 32 is either threadedly or fixably attached to a longitudinally elongated extension tube 46. In the preferred embodiment, extension tube 46 is threadedly connected to the top end of sensor tube 32 by means of connector collar 47. In the preferred embodiment, a plurality of pulley wheels 48 are rotatably mounted to a plate 49, the distance between the pulley wheels 48 being approximately the same as the outside diameter of the sensor tube 32, thereby positioning the annular grooves 50 of the pulley wheels 48 for receiving and guiding the extension tube 46, as will hereinafter be seen. As disclosed in FIG. 3, plate 49 comprises three pulley wheels 48 arranged in a triangular configuration. Plate 49 is connected by any suitable means, for example pivot rod 54, to a C-clamp 55 which is securably mounted to the side of the shaker box 17 or the suction tank 21. Pivot rod 54 is a generally L-shaped rod which is preferably fixably attached to C-clamp 55 on one end and preferably fixably attached to plate 49 on its other end, so that the extension tube 46 is permitted to pass through the space between pulley wheels 48, so that the annular grooves 50 of pulley wheels 48 guide extension tube 46, and therefore sensor tube 32, along a substantially vertical axis relative to the surface of the drilling fluid to have its density determined. A connector nipple 60, adapted for receiving an air supply conduit 62 is threadedly connected, preferably, to the top end of extension tube 46. Air supply conduit 62 is connected on one end to connector nipple 60 and on its other end to a source of pressurized air, which can be provided by the drilling rig 2 or a small air pump (not shown). An air regulator 64 is connected to the air supply conduit 62 for regulating the air entering the extension tube 46 and the sensor tube 32 via air supply conduit 62 at a pressure of approximately 3 p.s.i. The low pressure is used to maintain a constant flow of air through the extension tube 46 and the sensor tube 32 with a minimum amount of friction and the flow is maintained constant in each tube 46, 32 by means of flow meters 35 which are serially mounted to the air supply conduit 62 between air regulator 64 and the source of compressed air (not shown). Another conduit 66, is connected to air supply conduit 62 at some point above connector nipple 60, so that conduit 66 fluidly communicates with conduit 62. Conduit 66 is connected on its other end to a remote pressure recorder 68 and a pressure gauge 70 which are calibrated in inches of water, which is readily converted to pounds per gallon and/or pounds per cubic foot. Since the sensor 32 is preferably submersed 8.34 inches in the fluid to have its density determined, if the fluid is water, then the amount of air pressure required to maintain air flow in the sensor tube 32 and the extension tube 46 will read 8.34 in inches of water on the pressure gauge 70 and the pressure recorder 68. Since the weight of water is 8.34 pounds per gallons, then this 8.34 inches of water figure can be directly read as 8.34 pounds per gallon fluid density. Now, if the sensor tube 32 is submersed 8.34 inches in 18.0 pounds per gallon density drilling fluid, the amount of air pressure required to maintain air flow will be 18 inches of water as read on the pressure gauge 70 and the pressure recorder 68, and this pressure can be directly interpreted as 18.0 pounds per gallon mud weight.

The operation of the device is as follows:

1. The C-clamp 55 is securably mounted to the side of either the shaker box 17 or the suction tank 21, wherein the drilling fluid is contained, thereby substantially aligning the longitudinal axis of the space between the pulley wheels 48 with the vertical axis of the imaginary plane perpendicular to the surface of the drilling fluid to have its density determined;

2. The extension tube 46 is inserted in the space between the pulley wheels 48 so as to ride in the annular grooves 50 of the pulley wheels 48, the float 43 floating on the surface of the drilling fluid in the tank 21 or the shaker box 17, so that the sensor tube 32 is submersed at an 8.34 inch depth in the drilling fluid, the pulley wheels 48 ensuring that the extension tube 46 and the sensor tube 32 remain in a substantially vertical axis relative to the surface of the drilling fluid to have its density determined;

3. Compressed air is fed from the source of compressed air (not shown) and is regulated to a pressure of approximately 3 p.s.i. by means of air regulator 64 before flowing through air supply conduit 62 and through extension tube 46 into sensor tube 32; low pressure is used to maintain a constant flow of air through the tubes 46, 32 with a minimum amount of friction and the flow is maintained constant in each tube 46, 32 by means of flow meters 35;

4. If the drilling fluid is water, an air pressure of 8 inches of water will be necessary to create an equilibrium condition between the air in the sensor tube 32 and the drilling fluid to have its density determined, and this equilibrium condition can be observed as bubbles at the surface of the drilling fluid;

5. Because drilling fluid is generally denser than water, a greater air pressure, in inches of water, as readable on the pressure gauge 70, will be required in order to achieve an equilibrium condition between the air in the sensor tube 32 and the drilling fluid in the shaker box 17 or the suction tank 21; when the operator (not shown) of the device of the present invention observes bubbles at the surface of the drilling fluid, then this signifies that an equilibrium condition has occurred between the air in the sensor tube 32 and the drilling fluid to have its density determined; at the time that this equilibrium condition occurs, the density of the drilling fluid can be determined by reading the pressure gauge 70, and because of the manner in which the pressure gauge 70 is calibrated, this reading in inches of water is directly convertible into pounds per gallon, which is indicative of the density of the drilling fluid; remote pressure recorder 68 continuously records these readings.

Having now described a preferred embodiment of the present invention, what is claimed as invention is:

1. An apparatus for determining density of a drilling fluid in a fluid containing tank at an oil rig, comprising:

a. a single pneumatic tube submersed at a predetermined depth in said drilling fluid, said tube having at one end a check-valve means fluidly communicating with said drilling fluid in said tank, said tube further communicating with a source of pressurized air and a pressure recorder means at the other end;

b. air supply conduit means for connecting said pneumatic tube to said source of pressurized air;

c. conduit means for connecting said pneumatic tube to said pressure recorder means fluidly communicating with said air supply conduit means and said pneumatic tube;

d. means for constantly maintaining said pneumatic tube at said predetermined depth in said drilling fluid;

e. control means for delivering and maintaining a constant and equal rate of air flow into said tube;

f. readout means for displaying the density of the drilling fluid;

g. means for maintaining said pneumatic tube in substantially vertical alignment in relation to the surface of said drilling fluid, said means mounted at a distance above said means for maintaining said tube at said predetermined depth, said vertical alignment means comprising a pivot rod means connected to a fixation means attached to a side wall of said fluid containing tank at one end, extending perpendicularly in relation to said side wall inwardly in relation to said tank and having a vertically oriented plate attached at its other end, said vertical alignment means further comprising a plurality of annularly grooved wheels rotatably mounted on said plate and adapted to slidably engage said pneumatic tube in said grooves.

2. The apparatus of claim 1, wherein it further comprises recorder means for continuously recording the density of said drilling fluid.

3. The apparatus of claim 1, wherein said means for maintaining said tube at said predetermined depth in said drilling fluid comprises float means mounted to said tube.

4. The apparatus of claim 1, wherein said float means comprises a generally spherical, air-tight, floatable chamber mounted to said pneumatic tube.

5. The apparatus of claim 4, wherein said floatable chamber is adjustably mounted to said tube for maintaining said tube at a proper, pre-selected depth within said drilling fluid.

6. The apparatus of claim 5, wherein said floatable chamber is fixably mounted to said pneumatic tube.

7. The apparatus of claim 6, wherein said pneumatic tube further comprises a bell-shaped bottom end having a check valve mounted therein for preventing the upflow of said drilling fluid into said pneumatic tube.

8. The apparatus of claim 1, wherein said control means comprises an air regulator mounted to said air supply conduit in series with at least one flowmeter for maintaining a constant and equal rate of air flow into said tube.

9. The apparatus of claim 1, wherein said air flow is constant at approximately 3 p.s.i.

10. The apparatus of claim 1, wherein said tube is submersed at the predetermined depth of 8.34 inches in said drilling fluid.

11. The method of operation of the apparatus of claim 1, comprising the following steps:

a. submersing said pneumatic tube at a predetermined depth in said drilling fluid;

b. actuating said source of pressurized air to deliver pressurized air into said pneumatic tube, said control means maintaining a constant and equal rate of air flow into said tube;

c. observing the surface of said drilling fluid for air bubbles caused by the flow of pressurized air through said tube into said drilling fluid, said readout means displaying the density of the drilling fluid upon the occurrence of this condition of bubbles appearing at the surface of said drilling fluid.

* * * * *